United States Patent [19]
Dalton

[11] Patent Number: 6,138,046
[45] Date of Patent: Oct. 24, 2000

[54] DOSIMETRY PROBE

[75] Inventor: Brian Dalton, Santa Barbara, Calif.

[73] Assignee: Miravant Medical Technologies, Inc., Santa Barbara, Calif.

[21] Appl. No.: 09/295,246

[22] Filed: Apr. 20, 1999

[51] Int. Cl.[7] .............. A61B 6/00; A61B 17/36; A61N 21/00; G02B 6/02; G01J 3/00

[52] U.S. Cl. .............. 600/476; 607/88; 606/16; 385/123; 356/300

[58] Field of Search .................. 600/473, 471, 600/476, 477, 478; 607/88, 93, 94; 606/2, 7, 10, 11, 12, 13, 14, 15, 16, 17; 385/12, 13, 31, 32, 123, 124, 125, 126, 127; 356/300, 301, 318

[56] References Cited

U.S. PATENT DOCUMENTS

| | | | |
|---|---|---|---|
| 4,816,670 | 3/1989 | Kitamura et al. | 385/33 |
| 5,199,431 | 4/1993 | Kittrell et al. | 128/634 |
| 5,275,160 | 1/1994 | Lilge et al. | 128/634 |
| 5,349,954 | 9/1994 | Tiemann et al. | 128/634 |
| 5,481,113 | 1/1996 | Dou et al. | 250/341.1 |
| 5,483,958 | 1/1996 | Merberg et al. | 128/634 |
| 5,492,118 | 2/1996 | Gratton et al. | 128/633 |
| 5,529,065 | 6/1996 | Tsuchiya | 128/633 |
| 5,533,508 | 7/1996 | Doiron | 128/634 |
| 5,582,169 | 12/1996 | Oda et al. | 128/633 |
| 5,652,810 | 7/1997 | Tipton et al. | 385/12 |
| 5,693,043 | 12/1997 | Kittrell et al. | 606/15 |
| 5,728,092 | 3/1998 | Doiron et al. | 606/15 |
| 5,769,791 | 6/1998 | Benaron et al. | 600/473 |
| 5,807,261 | 9/1998 | Benaron et al. | 600/473 |
| 5,825,488 | 10/1998 | Kohl et al. | 356/342 |
| 5,836,883 | 11/1998 | Tsuchiya et al. | 600/476 |
| 5,911,017 | 6/1999 | Wach et al. | 385/12 |
| 5,925,034 | 7/1999 | Buckley et al. | 606/15 |

FOREIGN PATENT DOCUMENTS

WO 99/06113  2/1999  WIPO.

OTHER PUBLICATIONS

Pantelides, M.L. et al., "Photodynamic Therapy for Localised Prostatic Cancer: Light Penetration in the Human Prostate Gland," *The Journal of Urology*, vol. 143, Feb. 1990, pp. 398–401.

Whitehurt, C. et al., "Optimization of Multifiber Light Delivery for the Photodynamic Therapy of Localised Prostate Cancer," *Photochemistry and Photobiology*, vol 58, 1993, pp. 589–593.

Bays, Roland et al., "Light Dosimetry for Photodynamic Therapy in the Esophagus," *Lasers in Surgery and Medicine*, 1997, pp. 290–303.

Qun Chen, "Changes in In Vivo Optical Properties and Light Distributions in Normal Canine Prostate During Photodynamic Therapy," *Radiation Research*, vol. 147, 1997, pp. 86–91.

Lee, L.K. et al., "In situ Comparison of 665 nm and 633 nm Wavelength Light Penetration in the Human Prostate Gland," *Photochemistry and Photobiology*, 1995, vol. 62, No. 5, pp. 882–886.

*Primary Examiner*—Sam Paik
*Attorney, Agent, or Firm*—Bryan Cave LLP

[57] ABSTRACT

A dosimetry probe for monitoring light irradiation dosages and for providing irradiance measurements to monitor the application of light during a phototherapy procedure. The dosimetry probe includes a light delivery optical fiber operable to transmit optical radiation to target tissue and a plurality of dosimetry optical fibers substantially coextensive with the light delivery optical fiber, the distal ends of each of the dosimetry optical fibers arranged at a different axial distance from the light delivery optical fiber to provide irradiance measurements at a number of different axial distances. The dosimetry probe may include a safety feedback optical fiber to monitor the intensity of the treatment light independent of the influence of the optical properties of the target tissue. The dosimetry probe may also include a source dosimetry optical fiber for carrying a modulated dosimetry light signal, which can be selectively detected by means of frequency lock-in technology.

32 Claims, 7 Drawing Sheets

DOSIMETRY PROBE

FIELD OF THE INVENTION

The present invention relates generally to devices for monitoring and measuring light irradiation dosages applied to remote sites through optical fibers and, more particularly, to dosimetry probes, and, most particularly, to a fiber optic dosimetry probe for monitoring light irradiation during photodynamic therapy treatments.

BACKGROUND OF THE INVENTION

Light-based treatments (i.e., phototherapy) of many kinds are being used or considered for addressing a number of medical ailments. Phototherapy of diseased tissue includes various forms of treatment including photoablation, photodynamic therapy, or photocoagulation. In each of these, control of the treatment outcome relies on control of the dosage of light administered, as well as the dosage of any additional agents such as photosensitizers used in conjunction with the therapeutic light. Accurate measurement and monitoring of administered light dosage (i.e., dosimetry) is essential for comprehensive control of the process and preferably is available simultaneously with the application of the therapeutic light. Further, correct interpretations of dosimetric data are only possible within the context of an inclusive understanding of the relevant optical properties of the target tissue.

Photodynamic therapy (PDT) is an evolving treatment that employs the interaction between photoactive drugs and light of an appropriate wavelength to destroy diseased or malignant tissue. During a PDT procedure, one or more photosensitive molecules are administered within a target tissue of a patient and are then illuminated with phototherapeutic light having a wavelength operable for interacting with the photosensitive molecules in such a manner as to produce a photoactivated species of the molecules possessing molecules in such a manner as to produce a photoactivated species of the molecules possessing therapeutic properties. The photoactivated species that are formed either destroy cells or arrest physiological activity in the associated diseased tissue thereby effecting a treatment of the target tissue.

A problem associated with administering phototherapy in general, and photodynamic therapy in particular, is accurate dosimetry; that is, establishing when an effective dose of light has been administered to cure the diseased target tissue. For example, the amount of photodynamic therapy administered to a target tissue depends on the number of photoactivated species produced which, in turn, depends upon both the amount or concentration of photosensitizer accumulated within the tissue as well as the amount of light delivered to the photosensitizer. Thus, the photosensitive reaction, which is responsible for the therapeutic effects sought, is a second order reaction. In other words, the rate of formation of photoactivated therapeutic species within a target tissue undergoing phototherapy is proportional to both the intensity of light reaching the tissue and the concentration of photosensitive or photoreactive molecules within the diseased target tissue. Inaccurate light dosimetry can lead to either incomplete treatment of the diseased tissue, resulting in recurrence, or to significant damage to healthy tissue surrounding the diseased tissue. Accordingly, safe and effective application of photodynamic therapy requires accurate and adequate light delivery together with careful monitoring of the phototherapy irradiation.

Within a three-dimensional target tissue matrix, accurate monitoring of light dosage requires careful control of the positioning of the dosimetry fiber in order to yield accurate and reliable information, as the intensity of light fluence (i.e., irradiance) varies with the distance from the light source. The amount of therapeutic light delivered to the target tissue is, in general, inversely proportional to the square of the distance of the light source from the target tissue. That is, excluding light loss due to absorption or scattering of therapeutic light by non-target intervening media, the intensity of treatment light reaching a target tissue is inversely proportional to the square of the distance between the emission point of the light source and the target tissue. Due to relative uncertainty in the distance between a source of light (such as a light diffuser element) and the target tissue undergoing treatment, the quadratic reduction in the intensity of light reaching a target tissue with respect to the distance between the source of light and target tissue makes it difficult to establish the precise amount of light administered to a target tissue during phototherapy.

Another important factor in correctly monitoring and measuring the distribution of light are the specific optical properties of the target tissue. In order to reliably determine these optical properties, it is generally necessary to obtain a plurality of irradiance measurements, each taken at a unique and accurately known distance from the light source. In order to achieve this with existing technology, multiple fiber optic dosimetry probes are required, each individually and carefully placed within the target tissue.

Previously, fiber optic devices of many forms have been used for delivering light in medical treatments and therapies. Similar devices have also been used to gather dosimetric data from treatment sites. Conventionally, these light delivery and irradiance measurement devices have been separate units and have been brought together in cases where monitoring of light treatment has been desired. For example, a typical prior art method involves the insertion of an optical fiber to deliver light to the target tissue. Another optical fiber is inserted, typically via a different entry point, and used as a light detecting probe. In order to determine the light fluence distribution throughout the target tissue, measurements are made at several insertion points and/or at several insertion angles. The multiple insertion points and tracks must be measured and recorded in order to later calculate the distance from the end of the light delivery optical fiber and the light detecting probe at each measurement location. This method is unsuitable for a number of applications, for example when access to the target tissue is restricted.

In another prior art method, a light delivery and a light detector fiber are inserted into a sheath. During the treatment process, the light detector fiber may then be withdrawn in discrete steps, for example using a vernier stage, to allow light intensity readings to be made at different interfiber separation distances. This prior art method involves the use of a light delivery fiber and a single light detector fiber placed interstitially via a single point of entry in contrast to the other conventional method employing two separate systems, one for delivery of light, and the other(s) for detection of light penetration.

These prior art techniques suffer from significant disadvantages in addition to those previously mentioned. For example, they require time to adjust the placement of the detection fibers. The speed with which the light treatment may be applied and measured is important to reduce complications. Also, obtaining accurate placement of the detection fibers is difficult. Additionally, with prior art techniques there is need to accurately calculate the distance between the ends of the light delivery and light detection optical fibers.

Accordingly, there is a continuing need for an improved dosimetry probe adapted to sample the light incident upon a diseased target tissue undergoing phototherapy. Desirably, the dosimetry probe would monitor the photoactivation process in real-time so that the phototherapy process can be controlled and optimized for each individual application. A preferred probe would allow irradiance and light penetration measurements to be taken in-situ at precise displacement locations to determine the extent to which light penetrates the target tissue and allow the optical properties of the target tissue to be determined. It would also be desirable to combine the capabilities of light delivery, real-time dosimetry and measurement of the optical properties of target tissue into a single, easy-to-use probe.

SUMMARY OF THE INVENTION

In accordance with the present invention, a single fiber-optic device, which can be placed interstitially and has the ability to apply treatment light to the surrounding target tissue, while simultaneously providing real-time irradiance measurements, is fabricated from a number of optical fibers. The optical fibers include a light delivery optical fiber having a proximal end for coupling to a source of optical radiation and a distal end for placing near or into the target tissue. The light delivery optical fiber is operable to transmit light from its proximal end to its distal end to apply the treatment light to the target tissue. In most applications, the target tissue will absorb and/or scatter the applied treatment light. The dosimetry probe also includes a number of dosimetry optical fibers substantially coextensive with the light delivery optical fiber, each of the dosimetry optical fibers having a distal end placed at a different predetermined axial distance from the distal end of the light delivery optical fiber such that light scattered by the target tissue may be directed through the plurality of dosimetry optical fibers to proximal ends thereof for providing irradiance measurements to monitor the application of the treatment light to the target tissue.

The dosimetry probe of the present invention desirably includes features to enhance its performance and usefulness. For example, the dosimetry probe may incorporate a safety feature to monitor the intensity of the treatment independent of the influence of local tissue optics. Thus, a safety feedback optical fiber is arranged substantially coextensive with the light delivery optical fiber. The safety feedback optical fiber has a distal end placed near the distal end of the light delivery optical fiber and is adapted to receive light emitted from the light delivery optical fiber to measure the application of treatment light to the target tissue. The proximal end of the safety feedback optical fiber is preferably adapted for coupling to detector electronics adapted to generate irradiance measurements, and the safety feedback optical fiber conducts the received light emitted from the light delivery optical fiber to the proximal end of the safety feedback optical fiber and into the detector electronics.

In another embodiment of the present invention, the dosimetry probe accepts and transmits a separate, modulated dosimetry light signal, which can be selectively detected by means of frequency lock-in technology to increase the signal-to-noise ratios and to broaden the dynamic ranges of the dosimetry signals. A dosimetry source optical fiber is arranged substantially coextensive with the light delivery optical fiber and has a proximal end for coupling to a light source generating a modulated dosimetry signal. The dosimetry source optical fiber is adapted to transmit the modulated dosimetry signal to a distal end of the dosimetry source optical fiber for emission into the target tissue, wherein the target tissue absorbs and/or scatters the modulated dosimetry signal. The modulated dosimetry signal scattered by the target tissue may be detected by the dosimetry optical fibers and used to further analyze the optical properties of the target tissue and the application of treatment light.

Another embodiment of the present invention includes a light delivery and measurement assembly which includes the above-described dosimetry probe, a light source optically coupled to the proximal end of the light delivery optical fiber such that treatment light from the source can be directed through the light delivery optical fiber to the target tissue, and detector electronics adapted to generate irradiance measurements based on the light scattered from the target tissue.

The present invention also includes a method for applying treatment light to a target tissue and for providing irradiance measurements to monitor the application of the treatment light to the target tissue. The method includes the steps of providing one of the above-described dosimetry probes and placing the distal end of the dosimetry probe in optical communication with the target tissue. A source of optical radiation generating the treatment light is then coupled to the proximal end of the light delivery optical fiber such that the treatment light is transmitted through the light delivery optical fiber to irradiate the target tissue, wherein the target tissue absorbs and scatters the treatment light. The light scattered by the target tissue in response to the irradiation thereof is then received by the distal end of the plurality of dosimetry optical fibers and delivered to the proximal end of each of the plurality of dosimetry optical fibers. The scattered light is then detected and analyzed to provide irradiance measurements to monitor the application of the treatment light to the target tissue.

Furthermore, the present invention includes a novel method for fabricating the dosimetry probe. First, the light delivery optical fiber is inserted into a sheath. Then, each one of the dosimetry optical fibers is inserted into the sheath such that the dosimetry optical fibers at least partially concentrically surround the light delivery optical fiber. Finally, each of the dosimetry optical fibers is retracted to predetermined axial distance from the distal end of the light delivery optical fiber.

BRIEF DESCRIPTION OF THE DRAWINGS

To facilitate further discussion of the invention, the following drawings are provided in which.

These drawings are for illustrative purposes only and should not be used to unduly limit the scope of the claims.

DETAILED DESCRIPTION OF THE INVENTION

The dosimetry probe of the present invention is a single fiber-optic device, which can be placed interstitially and has the ability to apply treatment light to the surrounding target tissue, while simultaneously providing real-time irradiance measurements. These real-time irradiance measurements can be used to determine and monitor optical properties of the target tissue, such as the coefficient of absorption, which is the probability per unit length of tissue of a photon being absorbed by the tissue, the coefficient of scattering, which represents the probability per unit length of tissue of a photon being scattered, and the effective coefficient of attenuation. The dosimetry probe may also include a self-monitoring feature which feeds back a sample of the emitted light taken at the point of emission in order to assure the integrity of the treatment light delivered. Optionally, an additional light delivery fiber may be included to provide a modulated dosimetry signal, to be selectively detected by means of frequency lock-in technology. This optional feature increases the signal-to-noise ratios of the dosimetry signals as well as broadens their dynamic range.

Figure 1:
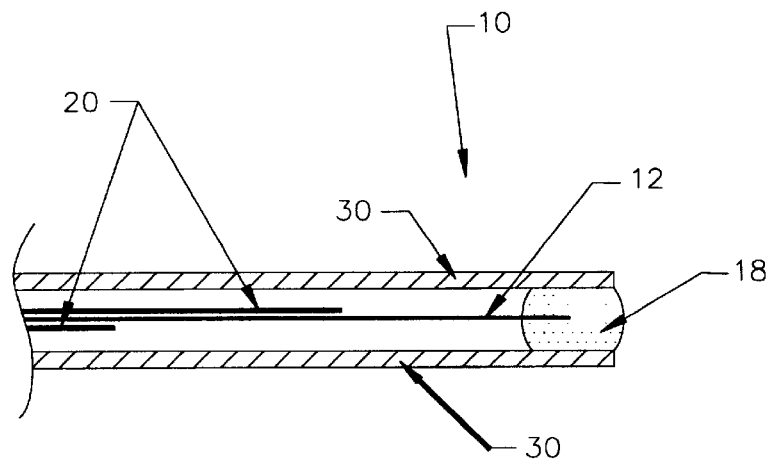
FIG. 1 is a longitudinal sectional view of the distal end of the dosimetry probe of the present invention showing the light delivery optical fiber and a plurality of dosimetry optical fibers.

FIG. 1 shows the preferred embodiment of the dosimetry probe 10 of the present invention in a broken longitudinal sectional view. The distal end of the dosimetry probe 10 shown in FIG. 1 is designed for placement or insertion near or into a target tissue of a patient. For example, the distal end of the dosimetry probe 10 may be inserted into the prostate gland of a patient undergoing a photodynamic therapy procedure.

The dosimetry probe 10 includes a light delivery optical fiber 12 designed to deliver treatment light, originating from a source of optical radiation coupled to its proximal end, to its distal end for application to the target tissue. While the light delivery optical fiber 12 may include any form of light conduit, the fiber 12 preferably has a core capable of carrying optical radiation and a cladding fabricated from a material having a lower index of refraction than the core to confine the radiation. One preferred light delivery optical fiber 12 comprises a fused silica core (capable of transmitting light of wavelengths in the range of 600–700 nm), surrounded by a silica cladding. The core may be sized to be in the range of 200–400 microns in diameter, and the cladding may be 20–40 microns thick. Of course, those skilled in the art will appreciate that other materials and sizes may be used for the light delivery optical fiber 12 and are within the scope of the present invention. The light delivery optical fiber 12 may also include a jacket or buffer to strengthen the fiber 12, such as a thin, chemically bonded, polyimide coating. The use of a thin polyimide coating on the light delivery optical fiber 12, as well as the other optical fibers included in the dosimetry probe 10, allows the probe 10 to be relatively small in cross-sectional area, a desired feature. The jacket may range in size from 20–30 microns thick.

The distal end of the light delivery optical fiber 12 preferably has a cleaved or polished flatcut tip from which the optical radiation is emitted. Alternatively, a conventional isotropic light diffusing tip may be attached to the light delivery optical fiber 12. Acceptable optical fibers for use as the light delivery optical fiber 12 may be obtained from Meteor Optics.

The length of the light delivery optical fiber 12 is chosen so that its distal end can be positioned near or in a desired, remote target tissue (e.g., in vivo) with its proximal end extending out of the patient for connection to a source of optical radiation. Light traveling through the light delivery optical fiber emerges from the distal end and illuminates surrounding target tissue, resulting in subsequent absorption and scattering of the light by the tissue. When the dosimetry probe 10 is used in conjunction with a PDT procedure, the treatment light delivered by the light delivery optical fiber 12 may initiate the chemical reaction of photosensitizers previously injected or absorbed into the target tissue.

A plurality of dosimetry optical fibers 20 are disposed in the dosimetry probe 10 coextensive with the light delivery optical fiber 12. Each of the dosimetry optical fibers 20 preferably terminates in a distal end that is placed at or near the distal end of the light delivery optical fiber 12. Each dosimetry optical fiber 20 is of similar construction to the light delivery optical fiber 12 and preferably is composed of a core surrounded by a thin cladding formed from a material having a lower index of refraction than the core. For example, the core may be about 100 microns in diameter, and the cladding may be about 10 microns thick. The dosimetry source fibers 20 may be substantially smaller in cross-section than the light delivery optical fiber 12, because they are not required to carry large amounts of optical power. The dosimetry optical fibers 20 are preferably all of the same size and type, although differing size and type fibers may be used.

The dosimetry optical fibers 20 must be able to accept optical radiation at their distal ends and transmit most of such received optical radiation to their proximal ends. Thus, the distal ends of the dosimetry optical fibers 20 preferably have a large numerical aperture (NA) to accept light radiation from a wide angle of acceptance. The tips at the distal ends of the dosimetry optical fibers 20 are preferably cleaved or polished flatcut with an acceptance angle (i.e., the maximum angle (half-angle) of incidence of light on the end of the optical fiber which can be transmitted by the fiber) of about 24°. The dosimetry optical fibers may operate in an isotropic fashion because the scattering nature of the surrounding tissue general randomizes the photon paths over a relatively short radial distance. Thus, if the target tissue (e.g., a prostate gland) has a radiance field that is generally isotropic, dosimetry fibers 20 having smaller NAs may be used.

The dosimetry optical fibers 20 preferably operate as isotropic light-receiving probes (i.e., have an isotropic pick-up pattern) and are used to monitor the light incident the distal ends thereof and propagated through the target tissue. Thus, the scattered light returning from the target tissue enters the distal ends of the dosimetry optical fibers 20, is conducted back along the fibers and exits the proximal ends of the fibers 20, where it may be analyzed using appropriate detector electronics. The detector electronics may include various conventional elements, such as photodiodes, multi-channel optical receivers, power meters, a spectral analyzer, and the like, which are integrated together in a known manner.

Figure 2:
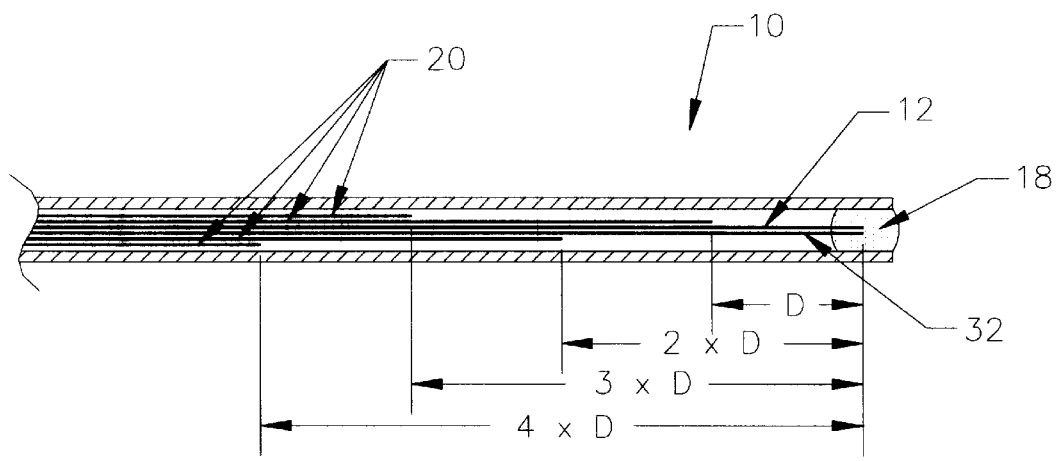
FIG. 2 is a longitudinal sectional view of the distal end of the dosimetry probe illustrating the axial displacement of the plurality of dosimetry optical fibers.

The distal ends of the dosimetry optical fibers 20 are arranged at varying axial distances from the distal end of the light delivery optical fiber 12. Preferably, the distal ends of the dosimetry optical fibers 20 are arranged in staggered formation back along the distal portion of the dosimetry probe 10 at regular intervals that are carefully controlled at the time of manufacture as shown in FIG. 2. Arranging the dosimetry optical fibers 20 at differing distances from the distal end of the light delivery optical fiber 12 allows measurements of the light fluence profile as a function of distance from the emission source of treatment light (i.e., the distal end of the light delivery optical fiber 12). The placement of the dosimetry optical fibers 20 axial to the light delivery optical fiber 12 generally reduces the ability of the dosimetry fibers to pick up the strongly forward biased light directly emitted from the light delivery optical fiber 12. Thus, the detected light will be an accurate representation of the light fluence rate for an isotropic light distribution. The distance increments between the distal end of each dosimetry optical fiber 20 (shown as D in FIG. 2) is preferably uniform and is selected based on the total number of dosimetry optical fibers included in the probe 10 and the desired range and resolution of the irradiance measurements. The incremental distances may also be selected based on the specific purpose of the measurements as well as the type of tissue being measured. As it is generally difficult to sense light scattered by the target tissue over distances more than a few centimeters, a preferred arrangement of dosimetry optical fibers 20 would be for the distal ends of the dosimetry optical fibers 20 to be placed over the distal 1.5 cm of the dosimetry probe 10. As the equations conventionally used to determine the optical properties of target tissue require at least five data points, at least five dosimetry optical fibers 20 would preferably be included in the dosimetry probe, having their distal ends separated axially by approximately 3 mm each. An appropriately designed and adequately sensitive detector electronics and signal processing system may be able to accurately discern signals at distances greater than 1.5 cm, providing additional data (beyond the requisite five data points) for tissue optics characterization and treatment monitoring. Alternatively, the distance between the individual dosimetry optical fibers 20 may be reduced, e.g., to 2 mm, in order to provide finer spatial resolution of the irradiance vs. distance data.

The dosimetry optical fibers 20 provide irradiance measurements at incremental distances from the light delivery optical fiber 12, allowing detailed photometric monitoring of the treatment zone within the target tissue. The arrangement of dosimetry optical fibers 20 also provides irradiance v. distance data, which can be used to calculate the optical properties of the target tissue (i.e., modeling how light is transported through the tissue). These optical properties may be determined from the real-time irradiance measurements using conventional techniques based on the mathematical models of light traveling through a medium. For example, based on diffusion theory, an approximate expression for the intensity of light (irradiance) vs. distance from the light source is given by the equation:

$$\phi(r) = \frac{P\mu_{Eff}^2}{4\pi r \mu_a} e^{-\mu_{Eff} r} \qquad \text{Eq. 1}$$

where:
r=distance from light source (i.e., the distal end of the light delivery optical fiber)
φ(r)=irradiance at distance r
P=power emitted by light source
$\mu_{Eff}$=effective coefficient of attenuation
$\mu_a$=coefficient of absorption And $\mu_{Eff}$ is derived as:

$$\mu_{Eff} = \sqrt{3\mu_a(\mu_a + \mu_s')} \qquad \text{Eq. 2}$$

where:

$\mu_s'$=reduced coefficient of scattering

Based on these relationships, $\mu_{Eff}$, $\mu_a$ and $\mu_s'$ can be calculated from a series of irradiance values measured at known distances by means of the following equations:

$$\mu_{Eff} = \frac{1}{r_2 - r_1} \ln\left(\frac{r_1 \phi_1}{r_2 \phi_2}\right) \qquad \text{Eq. 3}$$

$$\mu_a = \frac{P\mu_{Eff}^2}{4\pi r \phi(r)} e^{-\mu_{Eff} r} \qquad \text{Eq. 4}$$

$$\mu_s' = \frac{\mu_{Eff}^2}{3\mu_a} - \mu_a \qquad \text{Eq. 5}$$

As can be seen, Eq. 3 relies on only two data points to estimate $\mu_{Eff}$. A more accurate determination can be achieved by fitting the model of Eq. 1 to multiple (i.e., more than two) data points using a nonlinear or multivariate technique (e.g., Monte Carlo), wherein the parameters $\mu_{Eff}$ and $\mu_a$ are varied randomly until a sufficiently close fit is achieved.

Figure 3A:
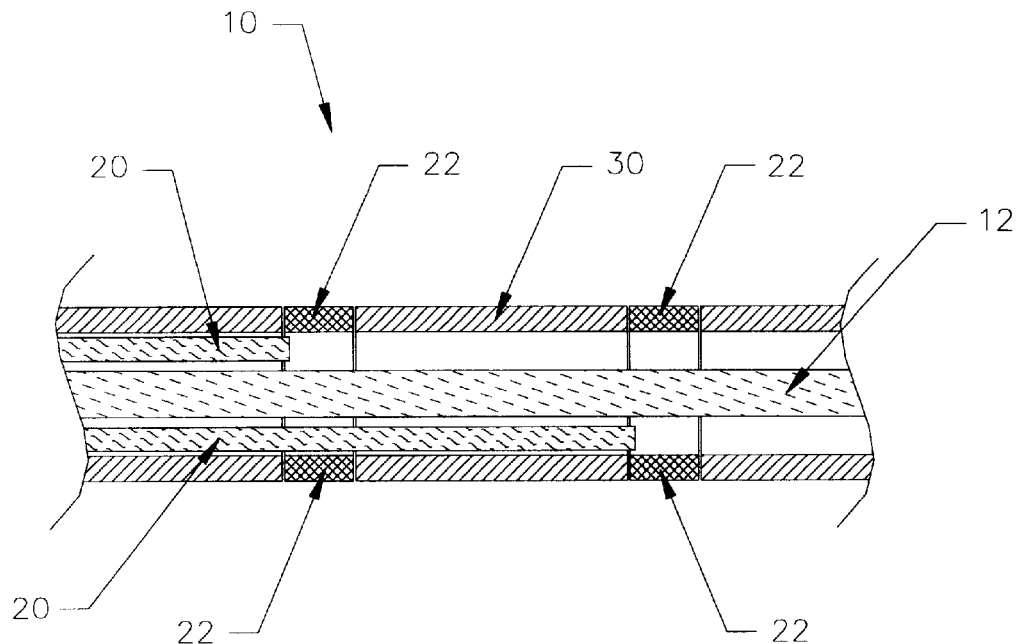
FIG. 3 is two sectional views of the dosimetry probe showing an opaque sheath having transparent windows therein.

The light delivery optical fiber 12 and the dosimetry optical fibers 20 are preferably housed in a flexible, tubular plastic sheath 30. The distal end of the light delivery optical fiber 12 is preferably placed within the sheath 30 such that the tip of the fiber 12 is just inside the distal end of the sheath 30. For example, the distance between the distal end of the sheath 30 and the distal end of the light delivery optical fiber 12 may be in the range of about 0.5 to 2.0 mm. The distal portion of the sheath 30 (i.e., the portion of the sheath surrounding the distal ends of the dosimetry optical fibers 20) is preferably either transparent or translucent such that the dosimetry optical fibers 20 may effectively sample the illumination of the surrounding target tissue. Alternatively, as shown in FIG. 3, the distal portion of the sheath may be relatively opaque and include a plurality of ports or windows 22 through which the dosimetry optical fibers 20 may receive the illumination from the tissue. FIG. 3a illustrates another embodiment wherein the windows 22 extend the entire circumference of the probe 10.

Figure 3B:
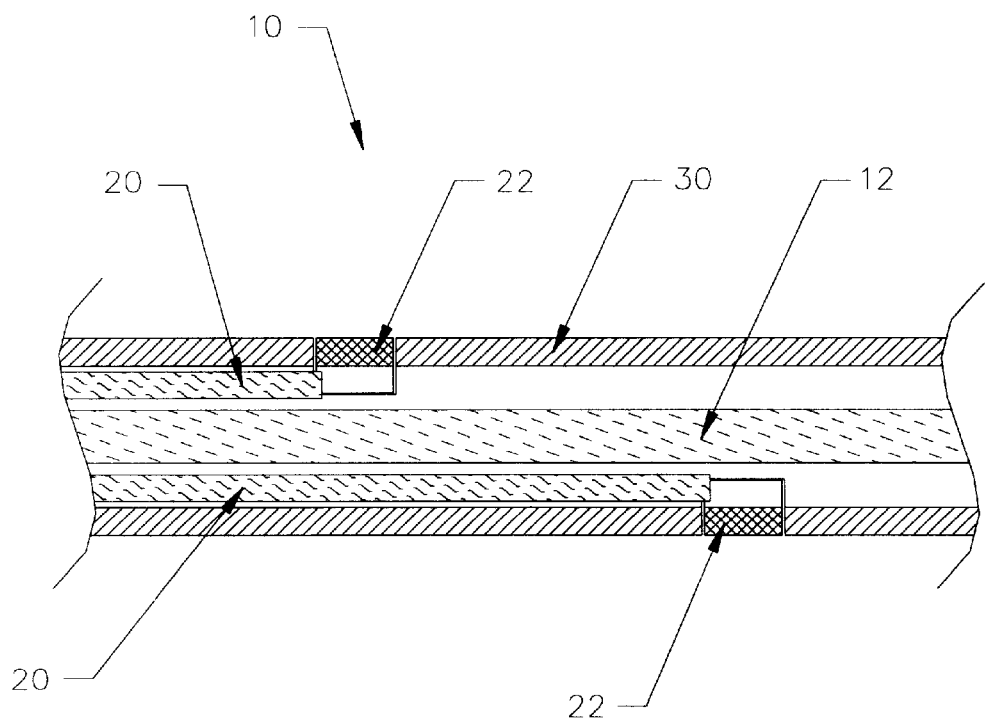

FIG. 3b illustrates an embodiment where the windows 22 are only contained on one side of the probe 10.

For the measurements derived from the light detected through the dosimetry optical fibers 20 to be accurate, the light received by the dosimetry optical fibers 20 must predominately arrive from the surrounding target tissue (and not from the light emitted from the adjacent light delivery optical fiber 12). In order prevent a significant portion of the light received by the dosimetry optical fibers 20 from originating with the light delivery optical fiber 12 through the sheath 30 by means of the sheath 30 acting as a light guide, the sheath 30 may contain either a small concentration of scattering material to disrupt this undesirable path or the sheath 30 may include opaque sections inserted between the light delivery optical fiber 12 and the dosimetry optical fibers 20. Alternatively, the light delivery optical fiber 12 may include an opaque jacket to prevent optical radiation from being emitted along the length of the light delivery optical fiber 12.

Figure 4:
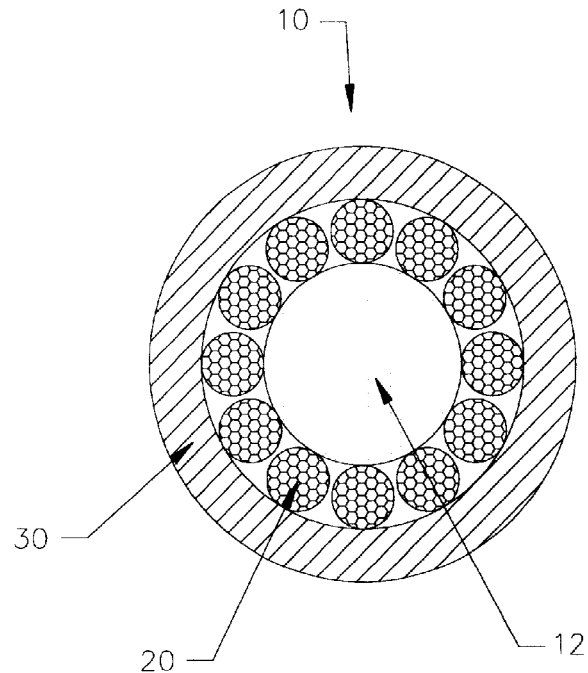
FIG. 4 is a cross sectional view of the dosimetry probe of FIG. 1 showing one arrangement of dosimetry optical fibers surrounding the light delivery optical fiber.

FIG. 4 illustrates one arrangement of the distal end of the dosimetry probe 10, showing the centrally located light delivery optical fiber 12 surrounded by a ring of twelve dosimetry optical fibers 20. In this construction, the dosimetry optical fibers 20 are preferably distributed spatially around the circumference of the light delivery optical fiber 12. Thus, the cross-sectional size of the dosimetry optical fibers 20 are chosen based on the cross-sectional size of the light delivery optical fiber 12. For example, using a 400 micron light delivery optical fiber 12 with a 470 micron overall outer diameter, twelve 100 micron dosimetry optical fibers 20 each with a 125 micron overall outer diameter form a substantially uniform ring surrounding the light delivery optical fiber 12. An alternative embodiment of the dosimetry probe 10, the distal end of which is shown in the cross-sectional view of FIG. 5, contains a centrally located light delivery optical fiber 12 surrounded by a ring of eight dosimetry optical fibers 20. This arrangement may include the use of a 200 micron light delivery optical fiber 12 with a 240 micron overall outer diameter and 100 micron dosimetry optical fibers 20 each with a 125 micron overall outer diameter. Of course, other geometries for the dosimetry probe 10, including those in which the dosimetry optical fibers 20 are not uniformly placed around a centrally-located light delivery optical fiber 12, but rather are asymmetrically arrayed within the dosimetry probe 10, may also be used without departing from the spirit and scope of the invention. The interior diameter of the sheath 30 must be large enough to contain the light delivery optical fiber 12 and the plurality of dosimetry optical fibers 20. For the arrangement illustrated in FIG. 5 (having a centrally located 200 micron light delivery optical fiber 12 and eight surrounding 100 micron dosimetry optical fibers 20) a sheath 30 having an interior diameter of about 20 mils would be appropriate.

In use, the distal portion of the dosimetry probe 10 is placed interstitially within a patient near or in a target tissue of interest. If the probe is used in conjunction with a PDT procedure, the patient likely previously received a dosage of an appropriate photosensitizing agent such as hematoporphyrin derivative (HpD), which is activated at 633 nm, tin ethyl etiopurpurin (SnET2), a second-generation photosensitizer maximally activated at 665 nm, or any other photosensitizer used in PDT treatments including purpurins, chlorins and phthalocyanines. A source of optical radiation generating the treatment light is coupled to the proximal end of the light delivery optical fiber 12. For example, a helium-neon (HeNe) laser operating in the range of about 200 to 500 mW, a 1000 mW diode laser, an argon-dye laser, or any other suitable laser capable of producing red light at a wavelength appropriate to activate the selected photosensitizers is attached using appropriate couplers to the proximal end of the light delivery optical fiber 12. The light from the laser may be coupled and focused into the proximal end of the light delivery optical fiber 12 using a lens system, such as a conventional SMA lens adapter and fiber termination assembly.

The application of therapeutic light to the target tissue will activate the photosensitizing agent within the target tissue giving rise to toxic species of oxygen and other chemical radicals and initiate tumor necrosis. During interstitial light application, photons are either scattered by tissue components or are absorbed by pigments within the target tissue. The scattered interstitial light enters the distal end of the dosimetry optical fibers 20 through the transparent sheath 30 (or through windows 22 therein) and passes down the axial length of the dosimetry fibers 20 to contact with, or be focused into, detector electronics. For example, the light output of each of the plurality of dosimetry optical fibers may be coupled, for example using an SMA connector, into a multi-channel light measuring device having a photodiode mounted near the proximal ends of the dosimetry optical fibers 20 to detect the scattered light. A light meter that provides an output proportional to the light fluence incident on the distal end of the dosimetry fibers may also be a component of the detector electronics to record the magnitude of the received light signals. An embodiment of the detector electronics is described below with reference to FIG. 8.

The dosimetry probe 10 of the present invention may be used to determine radiant energy fluence distributions by measuring the optical absorption and scattering properties of the target tissue at the wavelength of interest and then calculating the spatial distribution of fluence or absorbed energy. These optical properties may be determined from the real-time irradiance measurements using conventional techniques based on the mathematical models of light traveling through a medium, as described above. The inclusion of multiple dosimetry optical fibers 20 at different distances from the distal end of the light delivery optical fiber 12 allows for photometric measurements that can be used to calculate essential optical properties of the target tissue and facilitates their continual monitoring during treatment administration for use in investigating and documenting changes in these properties as treatment progresses.

As shown in FIG. 1, the distal end of the dosimetry probe 10 may include a scattering matrix 18 used as a diffusing medium, for example, an optically transparent bonding matrix impregnated with a controlled amount of light scattering particles such as alumina. The scatterer concentration in the bonding matrix is preferably optimized to provide an isotropic response. The inclusion of such a scattering matrix 18 provides a more uniform, isotropic output pattern, while reducing the potential for thermal buildup by rapidly dispersing the radiant energy as it exits the distal end of the light delivery optical fiber 12. The need to use a scattering matrix 18 may be less if the target tissue into which the dosimetry probe 10 is placed sufficiently scatters light. By using the scattering matrix 18, the dosimetry probe 10 exhibits isotropic light dispersion (i.e., the light emitted from the light delivery optical fiber 12 has a generally isotropic pattern) and has an isotropic sensing pattern (i.e., the dosimetry optical fibers 20 detect light in a substantially isotropic fashion).

The scattering matrix 18 preferably contains an amount of adhesive to secure the distal ends of the optical fibers in place. Thus, the scattering matrix 18 may extend down from the distal end of the dosimetry probe 10 at least as far as the dosimetry optical fiber 20 placed most remote from the distal end of the light delivery optical fiber 12.

Figure 5:
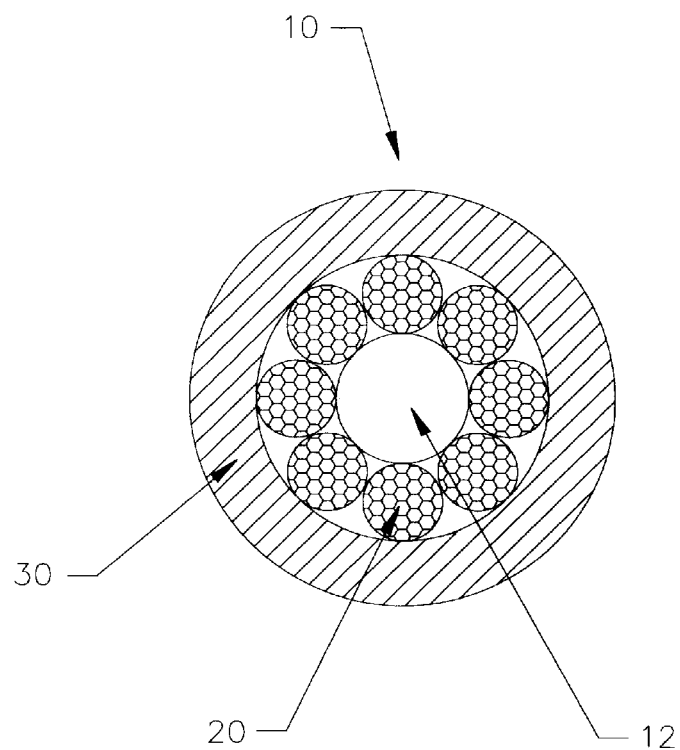
FIG. 5 is another cross sectional view of the dosimetry probe of FIG. 1 showing an alternative arrangement of dosimetry optical fibers surrounding the light delivery optical fiber.
Figure 6:
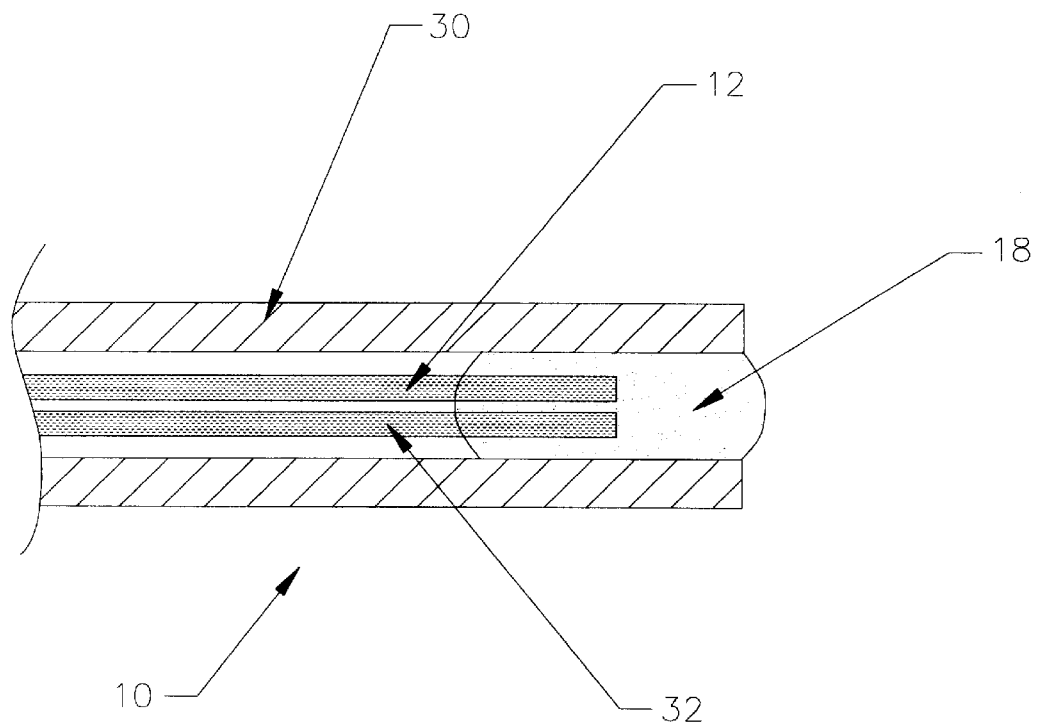
FIG. 6 is a longitudinal sectional view of the distal end of another preferred embodiment of the dosimetry probe showing the safety feedback optical fiber.

Various alternative embodiments of the dosimetry probe 10 are possible. For example, the dosimetry probe may also include a self-monitoring feature which feeds back a sample of the light emitted from the light delivery optical fiber 12 taken at the point of emission in order to assure the integrity of the treatment light delivered. FIG. 6 illustrates the dosimetry probe 10 including a safety feedback optical fiber 32. The safety feedback optical fiber 32 may be used to monitor the intensity of the treatment light independent of the influence of the optical properties of the target tissue. The safety feedback optical fiber 32 may be one of the optical fibers surrounding the light delivery optical fiber 12 as shown in FIGS. 4 and 5, or another separate optical fiber may be inserted into the dosimetry probe 10 as shown in FIG. 6. The safety feedback optical fiber 32 may be substantially smaller than the light delivery optical fiber 12 because it is not required to carry large amounts of optical power. The safety feedback optical fiber 32 preferably has a cleaved or polished flatcut tip.

The safety feedback optical fiber 32 is preferably positioned adjacent to the light delivery optical fiber 12 and is preferably potted into the scattering matrix 18. The safety feedback optical fiber 32 receives light as it is launched into the target tissue by the light delivery optical fiber 12. The close proximity between the distal ends of the light delivery optical fiber 12 and the safety feedback optical fiber 32 allows the light entering the feedback optical fiber 32 to derive overwhelmingly from the light emitted from the light delivery optical fiber 12 as compared to stray light from the surrounding target tissue. This ensures a high signal-to-noise ratio for the light received by the safety feedback optical fiber 32. The distal end of the safety feedback optical fiber 32 is preferably placed near (i.e., in both axial and radial distance) the distal end of the light delivery optical fiber 12. Preferably, the safety feedback optical fiber 32 touches the light delivery optical fiber 12 and the distal ends of these two fibers are placed within about 0.5 mm of each other. The safety feedback optical fiber 32 is primarily adapted to detect faults in the source of optical radiation connected to the proximal end of the light delivery optical fiber 12, or in the light delivery optical fiber 12. Detector electronics coupled to the proximal end of the safety feedback optical fiber 32 can detect such faults by sensing a change in the total light it detects. Because most of the light it detects is derived from the light delivery optical fiber 12, and because the safety feedback optical fiber 32 is seeking to detect relatively large changes in received optical power (i.e., light), any ambient light detected by the safety feedback optical fiber 32 will not significantly alter its performance. If the safety feedback optical fiber 32 detects a relatively large change in received optical radiation (e.g., at least 15–20%), then appropriate actions can be taken, such as warning the operator(s) of an unacceptable treatment condition, suspension of the treatment timing apparatus, deactivation of the light source(s), and the like.

Figure 7:
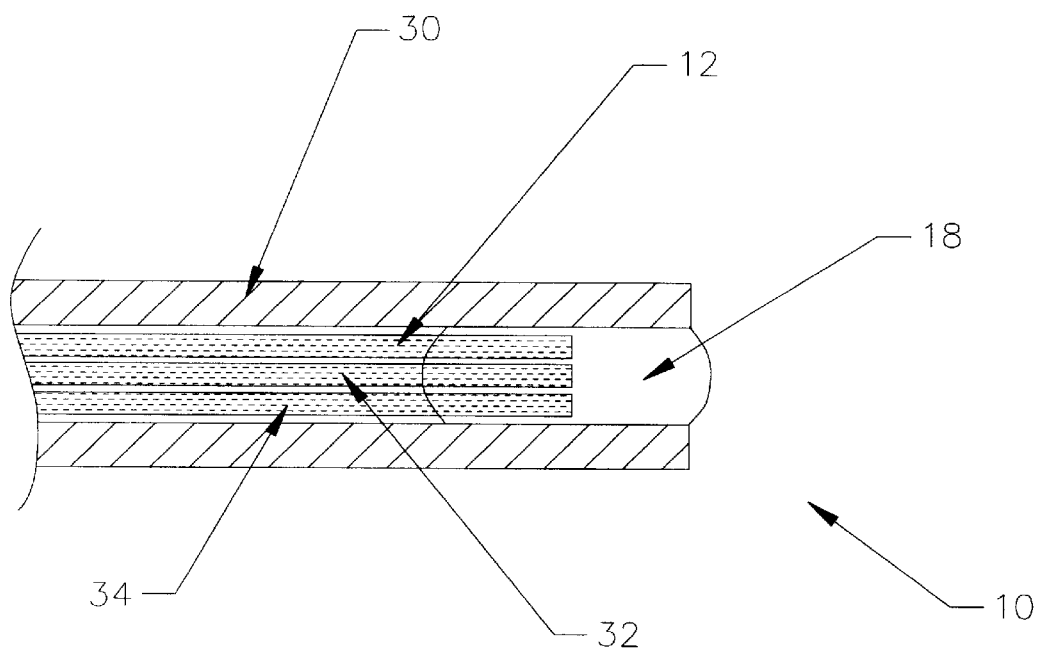
FIG. 7 is a longitudinal sectional view of the distal end of another preferred embodiment of the dosimetry probe showing the dosimetry source optical fiber.

In another embodiment of the present invention, as shown in FIG. 7, the dosimetry probe 10 may include a dosimetry source optical fiber 34 providing a secondary channel for delivering optical radiation into the target tissue. The dosimetry source optical fiber 34 may also be of similar configuration as the dosimetry optical fibers 20. In certain embodiments, the dosimetry source optical fiber 34 may be one of the optical fibers surrounding the light delivery optical fiber 12 as shown in FIGS. 4 and 5. Alternatively, a separate dosimetry source optical fiber 34 may be inserted into the dosimetry probe 10 as illustrated in FIG. 7.

Figure 8:
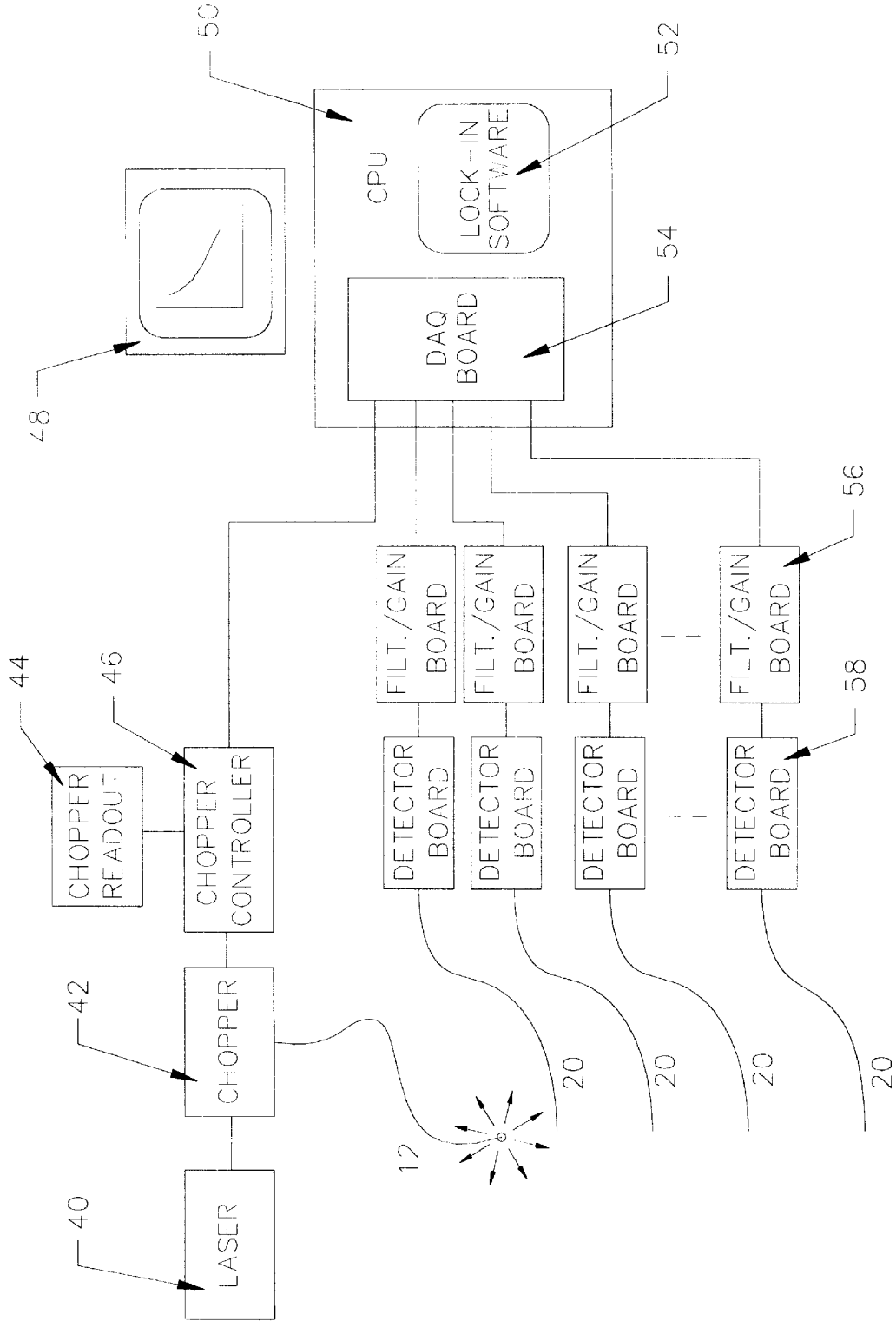
FIG. 8 is a diagram showing the principal elements of the detector electronics and devices used to generate a modulated light signal.

The dosimetry source optical fiber 34 is preferably adapted to carry a modulated dosimetry signal originating from a dosimetry light source coupled to its proximal end. For example, the dosimetry light source may be a second relatively low power laser, e.g., a laser operating at a power rating of about between 10–200 mW, or any other source of light, including room light. Referring to FIG. 8 (which illustrates one embodiment of detector electronics), the modulated signal may be created by chopping a continuous beam of light emitted from the laser 40 (or other light source) at a particular frequency using a frequency-controlled light chopping wheel 42 or an electronically switched liquid crystal shutter. In addition to providing a source of light that may be modulated for the dosimetry source optical fiber 34, the laser 40 may provide the treatment light coupled to the light delivery optical fiber 12 for use in any of the embodiments described herein. The light chopping wheel 42 modulates the laser 40 by periodically interrupting the light output of the laser 40. Thus, the light output incident on the proximal end of the dosimetry source optical fiber 34 varies between no light and the transmission of optical power. The modulation of the light chopping wheel 42 is controlled by the chopper controller 46, which controls the frequency of the light signal modulation and provides a reference signal to the data acquisition board 54. A display 44 may be coupled to the chopper controller 46 to provide an optical readout of the frequency of the light chopping wheel 42.

While a modulated dosimetry signal may be created by modulating the treatment light generated by the source of optical radiation coupled to the light delivery optical fiber 12, separating the functions of delivering treatment light and dosimetry prohibits a reduction in the power of treatment light necessitated by its modulation for dosimetry purposes. It is relatively easy to detect the received modulated dosimetry light signal via signal analysis techniques in the detector electronics coupled to the dosimetry optical fibers 20, even though other light may be included. The frequency of the modulated light may be in the range of greater than 60 Hz (to avoid ambient power line noise) to about 5000 Hz. Preferably, the frequency is selected to avoid 60 Hz, harmonics of 60 Hz, and is different than the frequency (and harmonics thereof) of any other light source operating in the system. Preferably, the wavelength of the modulated light signal is selected based on the type of photosensitizing drugs being used in the photodynamic therapy procedure. Thus, the optical properties of the target tissue are determined at the wavelength of the treatment light.

A portion of the modulated light signal emitted from the distal end of the dosimetry source optical fiber 34 is received by the dosimetry optical fibers 20. The dosimetry optical fibers 20 are coupled a plurality of detector boards 58, which sample and condition, i.e., amplify, the returned light signal. Each of the detector boards 58 is preferably coupled to a filter/range board 56, which filters the input light signal to reduce high frequency noise components. The filter/range board 56 may also provide adjustable amplification of the light signal to calibrate for various range settings (i.e., selectively amplifies the light signal returning on each dosimetry fiber 20 to account for its range from the distal end of the light delivery optical fiber 12). Each of the filter/range boards 56 are coupled into a data acquisition board 54, which resides in a CPU 50 and captures and digitizes the sampled light waveforms from each of its input channels, as well as the signal from the chopper controller 46. Through the use of conventional frequency lock-in software 52, also preferably located in the CPU 50, the modulated light signal can be extracted from the total light signal received from the dosimetry optical fibers 20, allowing the intensity of light reaching each dosimetry optical fiber 20 from the dosimetry source optical fiber 34 to be accurately determined. The frequency lock-in software 52 extracts the modulated signal from each dosimetry fiber 20 using a conventional digital frequency lock-in algorithm. The algorithm seeks the signal at a particular frequency and is thus able to isolate the dosimetry source signal from surrounding light noise. The CPU 50 provides processing capability and data storage capability and preferably includes analysis software to calculate the irradiance measurements and to determine the key optical properties of the medium under test (i.e., target tissue) by using appropriate mathematical models as previously described herein. The CPU preferably also supports and controls the data acquisition board 54 and provides for overall system control. The CPU 50 may be coupled to a CRT 48 to display data and provide a user interface.

In certain configurations, the optical fibers for the light delivery optical fiber 12, the dosimetry optical fibers 20, the safety feedback optical fiber 32, and the dosimetry source optical fiber 34 may be identical in size, shape, and construction, and may, therefore, be interchangeable in their functional roles.

Figure 9A:
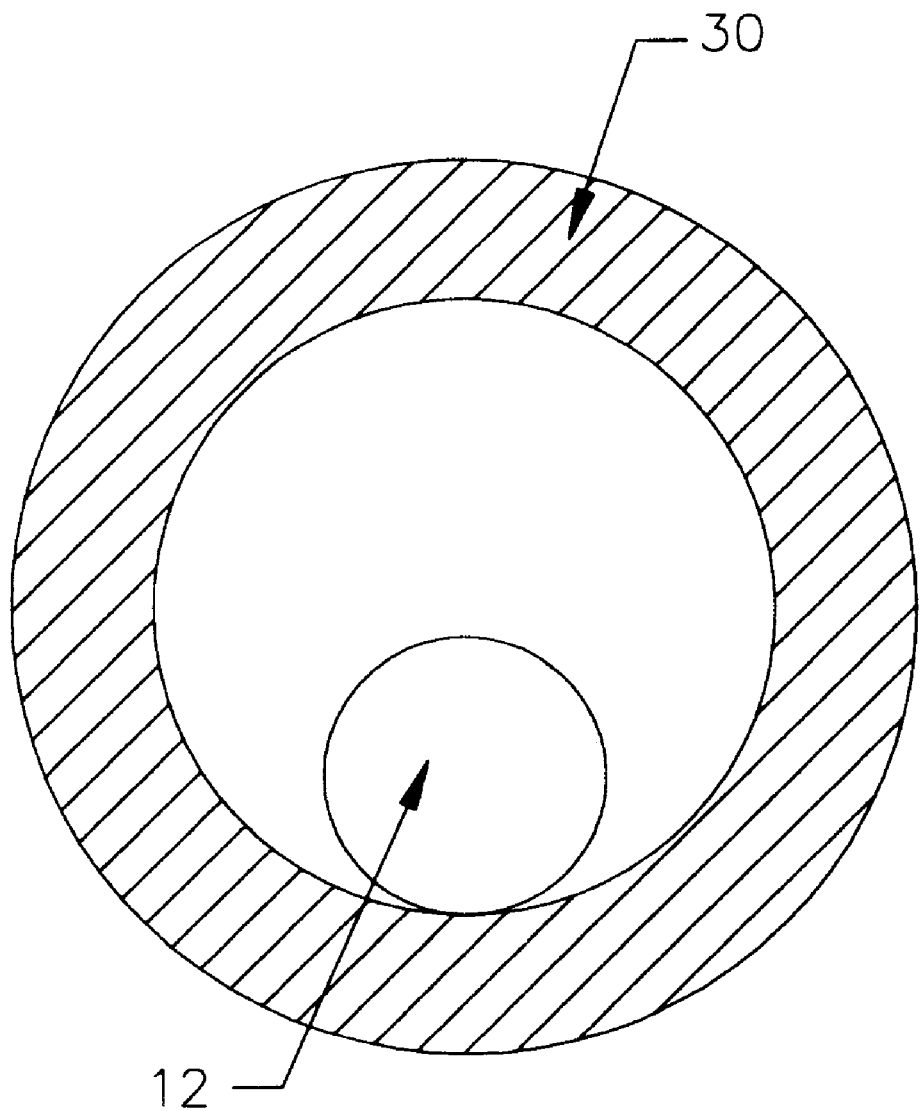
FIG. 9 illustrates a method of fabricating one embodiment of the dosimetry probe of the present invention.
Figure 9B:
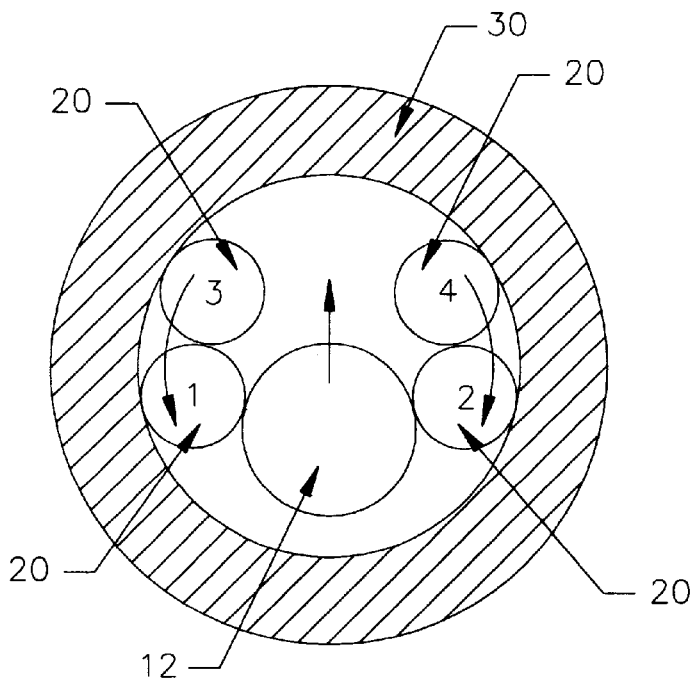
Figure 9C:
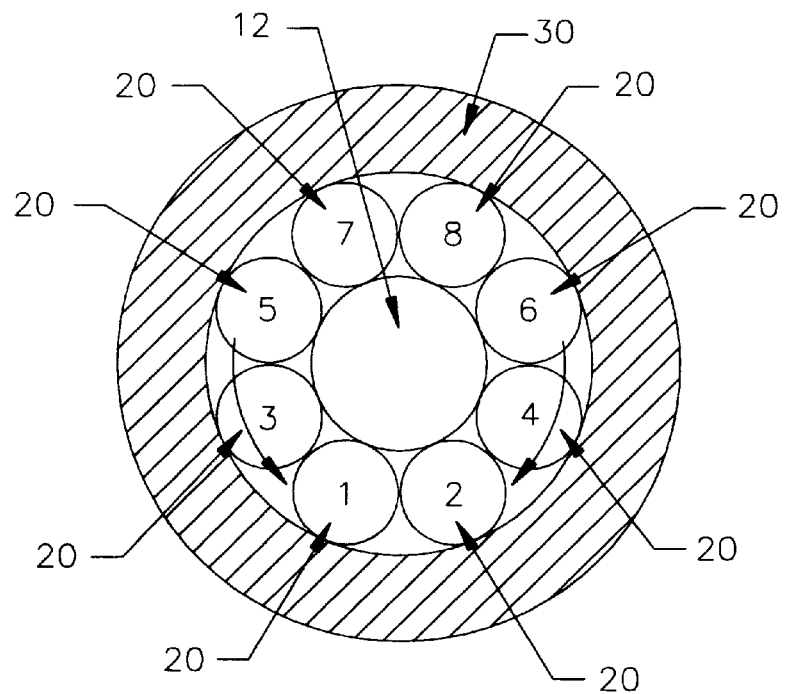

Various methods may be used to fabricate the dosimetry probe 10. For example, in fabricating the dosimetry probe 10 illustrated in FIG. 5, a short (i.e., about two inches) piece of sheath 30 having an interior diameter of about 20 mils is used. The nine fibers (including the single light delivery optical fiber 12 and the eight dosimetry optical fibers 20) must then be arranged within the sheath 30. As shown in FIG. 9a, the distal end of the light delivery optical fiber 12 is initially inserted approximately 2 mm into the sheath 30. The eight dosimetry optical fibers 20 are then inserted into the sheath 30, on alternating sides of the light delivery optical fiber 12, as illustrated in FIGS. 9b and 9c. As more dosimetry optical fibers 20 are added on top of others, the ones inserted earlier are forced down underneath the light delivery optical fiber 12, achieving a substantially concentric alignment. Alternatively, the several dosimetry optical fibers 20 may be inserted simultaneously into the sheath 30, and the light delivery optical fiber 12 may be subsequently inserted into the center of the sheath 30, between the dosimetry optical fibers 20, creating a substantially concentric pattern as desired. Initially, all of the eight dosimetry optical fibers 20 are inserted into the sheath 30 such that their distal ends approximately line up with the distal end of the light delivery optical fiber 12. The distal ends of all nine optical fibers must be arranged in their proper positions no more than about 2 mm into the sheath 30. Any optical fibers inserted beyond this point will tend to slip out of position due to the lack of lateral support from the other optical fibers within the sheath 30. Once all nine fibers are placed in the concentric pattern just inside (approximately 2 mm) the tip of the sheath 30, the fibers may be further inserted by moving all of the fibers substantially together, so that they can hold each other in place. All nine fibers are then further inserted into the predetermined maximum depth inside the sheath 30. The maximum depth is determined by the number of fibers used and the increment of distance used to provide axial separation, accounting for the optional use of one or more of the fibers as a safety optical feedback fiber 32 or a dosimetry source optical fiber 34 and allowing a reasonable amount of extra sheath length beyond the distal tip of the light delivery optical fiber 12 for insertion of the matrix injection device, the extra sheath length to be trimmed off after the matrix has been cured. After inserting all nine optical fibers to the maximum depth, individual dosimetry optical fibers 20 can be retracted to their final positions. For example, each of the eight dosimetry optical fibers 20 may be individually retracted a different predetermined amount such that their respective distal ends are at a predetermined axial distance from the distal end of the light delivery optical fiber 12. The position of the distal ends of the dosimetry optical fibers 20 may be monitored during this fabrication process by coupling a light source to the proximal ends of the dosimetry optical fibers 20. Preferably, a single light source is successively coupled to each individual dosimetry optical fiber 20 as it is being set in place. As it may be difficult to determine the location of the distal end of each of the dosimetry optical fibers 20 as light is emitted therefrom (because most of the light is emitted in a forward direction), it may be useful to insert the distal portion of the dosimetry probe 10 into a diffusing medium such as a water-based solution containing a lipid scatterer. This may not be necessary if the sheath 30 is formed from a diffusing material. A potting material, such as a scattering matrix 18 containing an amount of adhesive (such as transparent silicone or optical adhesive, impregnated with alumina scattering agents), is preferably injected into the distal portion of the dosimetry probe 10 before the dosimetry optical fibers 20 are placed into their final positions. The scattering matrix may be used to pot only the extreme distal tips of the optical fibers within the sheath 30, to create a pseudo-isotropic sphere, or an uncured scattering matrix having a lower viscosity may be used that extends down the distal portion of the dosimetry probe 10, thus potting all of the optical fibers in place without the need to heat shrink the sheath 30 onto the optical fibers. The method described herein may be used to fabricate any of the dosimetry probes described herein, including those having any number of dosimetry optical fibers, and those that may include a safety feedback optical fiber and/or a dosimetry source optical fiber.

The dosimetry probe 10, including any of its various embodiments described herein, may be used as a part of a light delivery and measurement apparatus. The apparatus comprises, as its principal elements, a dosimetry probe 10 adapted to have its distal portion placed interstitially near or into a target tissue, a source of optical radiation, and detector electronics. The dosimetry probe 10 may be configured in any of the embodiments previously described herein, including those having a safety feedback optical fiber and/or a dosimetry source optical fiber. The source of optical radiation is coupled to the proximal end of the light delivery optical fiber 12. For example, a 5 mW helium-neon (HeNe) laser, a 1000 mW diode laser, an argon-dye laser, or any other suitable light source capable of producing light at a wavelength appropriate to activate the selected photosensitizers is attached using appropriate couplers to the proximal end of the light delivery optical fiber 12. The detector electronics may include photodiodes, amplifiers, noise filters and signal buffers appropriate to the data acquisition hardware and software used, including those shown in FIG. 8.

The dosimetry probe described herein combines the functions of light delivery, real-time dosimetry, and photometric assessment of optical properties into a single fiber optic probe that can be placed interstitially via a single inducer needle, allowing all of the basic functions necessary for carefully controlled application of therapeutic light to be achieved through a single wound site. By incorporating the dosimetry fibers into the same device as the delivery fiber, and by controlling the distance of the tip of each dosimetry fiber to the tip of the delivery fiber during the manufacturing process, accurate dosimetry with respect to light propagation distance is not only assured but its achievement is rendered trivial. The dosimetry probe of the present invention allows real-time monitoring of treatment irradiation during photodynamic therapy procedures and real-time monitoring of the fluence distribution during such treatment. The inclusion of multiple dosimetry fibers at known distances allows for photometric measurements that can be used to calculate essential optical properties of the target tissue and facilitates their continual monitoring during treatment administration for use in investigating and documenting changes in these properties as treatment progresses. The monitoring can be used to adjust the light dose as the optical properties of the target tissue change during the course of the photodynamic therapy procedure.

Although the present invention has been described in considerable detail with reference to certain preferred versions thereof, other versions are possible without departing from the spirit and scope of the present invention. Therefore the scope of the appended claims should not be limited to the description of the preferred embodiments described herein. For example, the dosimetry probe of this invention may be used in any application where interstitial light delivery is required and can benefit from accurate and easy-to-implement dosimetry. Also, investigations of tissue optical properties in the absence of actual therapeutic light administration may be performed using the dosimetry probe described herein.

What is claimed is:

1. A dosimetry probe for applying treatment light to a target tissue and for providing irradiance measurements to monitor the application of the treatment light to the target tissue, the dosimetry probe comprising a plurality of optical fibers comprising:
   a light delivery optical fiber having a proximal end for coupling to a source of optical radiation generating the treatment light and a distal end for placing near or into the target tissue, the light delivery optical fiber being operable to transmit the treatment light from its proximal end to its distal end to apply the treatment light to the target tissue, wherein the target tissue absorbs and scatters the treatment light; and
   a plurality of dosimetry optical fibers arranged substantially coextensive with the light delivery optical fiber, each of the dosimetry optical fibers having a distal end placed at a different predetermined axial distance from the distal end of the light delivery optical fiber such that light scattered by the target tissue may be directed through the plurality of dosimetry optical fibers to proximal ends thereof for providing irradiance measurements to monitor the application of the treatment light to the target tissue.

2. The dosimetry probe of claim 1 wherein the plurality of dosimetry optical fibers at least partially concentrically surround the light delivery optical fiber.

3. The dosimetry probe of claim 1 wherein the distal end of each of the plurality of dosimetry optical fibers is placed at its predetermined axial distance from the distal end of the light delivery optical fiber based on a desired resolution of the irradiance measurements.

4. The dosimetry probe of claim 3 wherein the distal end of each of the plurality of dosimetry optical fibers is separated by an axial distance of about 3 mm from distal end of its adjacent dosimetry optical fibers.

5. The dosimetry probe of claim 1 wherein the proximal end of each of the plurality of dosimetry optical fibers is adapted for coupling to detector electronics adapted to generate the irradiance measurements, and wherein the plurality of dosimetry optical fibers conduct the received light scattered from the target tissue to the proximal ends of the plurality of dosimetry optical fibers and into the detector electronics.

6. The dosimetry probe of claim 1 wherein the target tissue has been medicated with a photosensitizing agent capable of being activated by the treatment light having a particular wavelength and wherein the source of optical radiation comprises a laser adapted to emit treatment light at the particular wavelength such that the treatment light is partially absorbed by the photosensitizing agent.

7. The dosimetry probe of claim 1 wherein the irradiance measurements may be used to determine the optical properties of the target tissue.

8. The dosimetry probe of claim 1 wherein the plurality of optical fibers further comprise a safety feedback optical fiber arranged substantially coextensive with the light delivery optical fiber, the safety feedback optical fiber having a distal end placed near the distal end of the light delivery optical fiber and is adapted to receive light emitted from the light delivery optical fiber to measure the application of treatment light to the target tissue.

9. The dosimetry probe of claim 8 wherein the distal end of the safety feedback optical fiber is placed in close proximity to the distal end of the light delivery optical fiber so that substantially all of the light received by the safety feedback optical fiber is derived from the treatment light emitted by the light delivery optical fiber.

10. The dosimetry probe of claim 9 wherein the safety feedback optical fiber further comprises a proximal end adapted for coupling to detector electronics adapted to generate the irradiance measurements, and wherein the safety feedback optical fiber conducts the received light emitted from the light delivery optical fiber to the proximal end of the safety feedback optical fiber and into the detector electronics.

11. The dosimetry probe of claim 1 wherein the plurality of optical fibers further comprise a dosimetry source optical fiber arranged substantially coextensive with the light delivery optical fiber and having a proximal end for coupling to a dosimetry light source generating a modulated dosimetry signal, the dosimetry source optical fiber adapted to transmit the modulated dosimetry signal to a distal end of the dosimetry source optical fiber for emission into the target tissue, wherein the target tissue absorbs and scatters the modulated dosimetry signal.

12. The dosimetry probe of claim 11 wherein the plurality of dosimetry optical fibers further receive the modulated dosimetry signal scattered by the target tissue.

13. The dosimetry probe of claim 12 wherein the modulated dosimetry signal may be detected using detector electronics using frequency lock-in techniques.

14. The dosimetry probe of claim 1 further comprising a sheath concentrically surrounding and housing the light delivery optical fiber and the plurality of dosimetry optical fibers.

15. The dosimetry probe of claim 14 wherein the sheath is transparent to allow the plurality of dosimetry optical fibers to effectively receive light scattered by the target tissue.

16. The dosimetry probe of claim 14 where the sheath is substantially opaque and comprises a plurality of transparent windows to allow the plurality of dosimetry optical fibers to receive the light scattered by the target tissue.

17. The dosimetry probe of claim 1 further comprising a transparent bonding matrix infused with a controlled amount of a scattering agent surrounding the distal end of the light delivery optical fiber so that the light emitted from the light delivery optical fiber has a substantially uniform, isotropic output pattern and so that the plurality of dosimetry optical fibers have a substantially isotropic pick-up pattern.

18. The dosimetry probe of claim 1 wherein the plurality of dosimetry optical fibers concentrically surround the light delivery optical fiber and the distal end of each of the plurality of dosimetry optical fibers is placed at its predetermined axial distance from the distal end of the light delivery optical fiber based on a desired resolution of the irradiance measurements, and wherein the plurality of optical fibers further comprise:
   a safety feedback optical fiber arranged substantially coextensive with the light delivery optical fiber, the safety feedback optical fiber having a distal end placed near the distal end of the light delivery optical fiber and adapted to receive light emitted from the light delivery optical fiber to measure the application of treatment light to the target tissue, and a proximal end adapted for coupling to detector electronics adapted to generate the irradiance measurements, and wherein the safety feedback optical fiber conducts the received light emitted from the light delivery optical fiber to the proximal end of the safety feedback optical fiber and into the detector electronics; and a dosimetry source optical fiber arranged substantially coextensive with the light delivery optical fiber and having a proximal end for coupling to a dosimetry light source generating a modulated dosimetry signal, the dosimetry source optical fiber adapted to transmit the modulated dosimetry signal to a distal end of the dosimetry source optical fiber for emission into the target tissue, wherein the target tissue absorbs and scatters the modulated dosimetry signal, wherein the plurality of dosimetry optical fibers further detect the modulated dosimetry signal scattered by the target tissue.

19. The dosimetry probe of claim 18 wherein the plurality of dosimetry optical fibers further receive the modulated dosimetry signal scattered by the target tissue.

20. The dosimetry probe of claim 19 wherein the modulated dosimetry signal may be detected using detector electronics using frequency lock-in techniques.

21. A light delivery and measurement assembly comprising:

a source of optical radiation generating treatment light;

a dosimetry probe for applying the treatment light to a target tissue, the dosimetry probe comprising a plurality of optical fibers comprising:

a light delivery optical fiber having a proximal end optically coupled to the source of optical radiation and a distal end for placing near or into the target tissue, the light delivery optical fiber being operable to transmit the treatment light from its proximal end to its distal end to apply the treatment light to the target tissue, wherein the target tissue absorbs and scatters the treatment light; and a plurality of dosimetry optical fibers arranged substantially coextensive with the light delivery optical fiber, each of the dosimetry optical fibers having a distal end placed at a different predetermined axial distance from the distal end of the light delivery optical fiber such that light scattered by the target tissue may be directed through the plurality of dosimetry optical fibers to proximal ends thereof for providing irradiance measurements to monitor the application of the treatment light to the target tissue; and detector electronics coupled to the proximal ends of each of the plurality of dosimetry optical fibers and adapted to receive the light scattered by the target tissue to generate irradiance measurements to monitor the application of the treatment light to the target tissue.

22. The light delivery and measurement assembly of claim 21 wherein the plurality of optical fibers further comprise a safety feedback optical fiber arranged substantially coextensive with the light delivery optical fiber, the safety feedback optical fiber having a distal end placed near the distal end of the light delivery optical fiber and is adapted to receive light emitted from the light delivery optical fiber to measure the application of treatment light to the target tissue.

23. The light delivery and measurement assembly of claim 21 further comprising a dosimetry light source generating a modulated dosimetry signal, and wherein the plurality of optical fibers of the dosimetry probe further comprises a dosimetry source optical fiber arranged substantially coextensive with the light delivery optical fiber and having a proximal end for coupling to the dosimetry light source generating a modulated dosimetry signal, the dosimetry source optical fiber adapted to transmit the modulated dosimetry signal to a distal end of the dosimetry source optical fiber for emission into the target tissue, wherein the target tissue absorbs and scatters the modulated dosimetry signal, and wherein the plurality of dosimetry optical fibers further detect the modulated dosimetry signal scattered by the target tissue.

24. The light delivery and measurement assembly of claim 23 wherein the plurality of dosimetry optical fibers further receive the modulated dosimetry signal scattered by the target tissue.

25. The light delivery and measurement assembly of claim 24 wherein the modulated dosimetry signal may be detected using detector electronics using frequency lock-in techniques.

26. The light delivery and measurement assembly of claim 21 wherein the dosimetry probe further comprises a sheath concentrically surrounding and housing the light delivery optical fiber and the plurality of dosimetry optical fibers.

27. The light delivery and measurement assembly of claim 26 wherein the sheath is transparent to allow the plurality of dosimetry optical fibers to effectively receive light scattered by the target tissue.

28. The light delivery and measurement assembly of claim 26 where the sheath is substantially opaque and comprises a plurality of transparent windows to allow the plurality of dosimetry optical fibers to receive the light scattered by the target tissue.

29. A method for applying treatment light to a target tissue and for providing irradiance measurements to monitor the application of the treatment light to the target tissue comprising the steps of:

providing a dosimetry probe having a plurality of optical fibers comprising:

a light delivery optical fiber having a proximal end for coupling to a source of optical radiation generating the treatment light and a distal end for placing near or into the target tissue, the light delivery optical fiber being operable to transmit the treatment light from its proximal end to its distal end to apply the treatment light to the target tissue; and a plurality of dosimetry optical fibers arranged substantially coextensive with the light delivery optical fiber, each of the dosimetry optical fibers having a distal end placed at a different predetermined axial distance from the distal end of the light delivery optical fiber such that light scattered by the target tissue may be directed through the plurality of dosimetry optical fibers to proximal ends thereof for providing irradiance measurements to monitor the application of the treatment light to the target tissue;

placing the distal end of the dosimetry probe in optical communication with the target tissue;

coupling the source of optical radiation generating the treatment light to the proximal end of the light delivery optical fiber such that the treatment light is transmitted through the light delivery optical fiber to irradiate the target tissue, wherein the target tissue absorbs and scatters the treatment light;

receiving light scattered by the target tissue in response to the irradiation thereof with the distal end of the plurality of dosimetry optical fibers and delivering the received light to the proximal end of each of the plurality of dosimetry optical fibers;

detecting the light delivered to the proximal end of each of the plurality of dosimetry optical fibers; and analyzing the detected light to provide irradiance measurements to monitor the application of the treatment light to the target tissue.

30. The method of claim 29 wherein the plurality of optical fibers of the provided dosimetry probe further comprise a dosimetry source optical fiber arranged substantially coextensive with the light delivery optical fiber, the dosimetry source optical fiber adapted to transmit a modulated dosimetry signal to a distal end of the dosimetry source optical fiber for emission into the target tissue, wherein the target tissue absorbs and scatters the modulated dosimetry signal, the method further comprising the steps of:

coupling a dosimetry light source generating the modulated dosimetry signal to the proximal end of the dosimetry source optical fiber;

receiving the modulated dosimetry signal scattered by the target tissue with the distal end of plurality of dosimetry optical fibers and delivering the received light to the proximal end of each of the plurality of dosimetry optical fibers; and analyzing the modulated dosimetry signal using detector electronics using frequency lock-in techniques to further monitor the application of the treatment light to the target tissue.

31. A method of fabricating the dosimetry probe of claim 1 comprising the steps of:

(a) providing a sheath;

(b) inserting the light delivery optical fiber into the sheath;

(c) inserting one of the plurality of dosimetry optical fibers into the sheath;

(d) repeating step (c) until all of the plurality of dosimetry optical fibers are inserted into the sheath such that the dosimetry optical fibers at least partially concentrically surround the light delivery optical fiber; and (e) retracting each of the plurality of dosimetry optical fibers to their predetermined axial distance from the distal end of the light delivery optical fiber.

32. The method of claim 31 further comprising the step of coupling a light source to the proximal ends of each of the plurality of dosimetry optical fibers during step (e) to monitor the retraction of the plurality of dosimetry optical fibers to assist in placing the fibers at their predetermined axial distances.

* * * * *